United States Patent [19]

Michal et al.

[11] 4,229,529

[45] Oct. 21, 1980

[54] PROCESS FOR DETERMINING FORMATE AND REAGENT THEREFOR

[75] Inventors: Gerhard Michal, Tutzing; Rolf Laube, Weilheim; Albert Röder, Seeshaupt; Walter Schneider, Weilheim, all of Fed. Rep. of Germany

[73] Assignee: Boehringer Mannheim GmbH, Mannheim, Fed. Rep. of Germany

[21] Appl. No.: 880,823

[22] Filed: Feb. 23, 1978

[30] Foreign Application Priority Data

Mar. 18, 1977 [DE] Fed. Rep. of Germany ....... 2712004

[51] Int. Cl.$^2$ ............................................ G01N 31/14
[52] U.S. Cl. ..................................................... 435/26
[58] Field of Search .......................... 195/103.5 R, 99; 435/26

[56] References Cited

FOREIGN PATENT DOCUMENTS 2013700 10/1971 Fed. Rep. of Germany .

OTHER PUBLICATIONS

Bergmeyer, *Methods of Enzymatic Analysis*, Academic Press, Inc., New York, (1974), pp. 1551-1555.
Chemical Abstracts 84:101328c (1976), pp. 217-218.
Chemical Abstracts 79:13956x (1973) p. 67.
Fujii et al., *Agr. Biol. Chem.* vol. 36, No. 13 (1972), pp. 2297-2306.

*Primary Examiner*—Esther M. Kepplinger
*Attorney, Agent, or Firm*—Sprung, Felfe, Horn, Lynch & Kramer

[57] ABSTRACT

Formate, or compounds convertible into formate, is determined by reacting same in the presence of formate dehydrogenase (FDH) and of a hydrogen acceptor, e.g., NAD, wherein the formate dehydrogenase is from *Candida boidinii* DSM 941, to result in stoichiometric reactions. The process can be used for the removal of formate from solutions containing same.

14 Claims, No Drawings

PROCESS FOR DETERMINING FORMATE AND REAGENT THEREFOR

The present invention is connected with a process for the determination or removal of formate by reaction in the presence of formate dehydrogenase and by a hydrogen acceptor.

The determination of formate with the help of formate dehydrogenase from *Pseudomona oxalaticus* in the presence of a hydrogen acceptor, such as nicotinamide-adenine-dinucleotide (NAD) is known, for example from H. U. Bergmeyer, *Methoden der enzymatischen Analyse*, 3rd edition, pp. 1597–1600, pub. Verlag Chemie, Weinheim, 1974. However, a disadvantage of the use of this enzyme is that NADH formation is not stoichiometric with the formate consumption, which is attributed to two side activities of formate dehydrogenase (FDH) which result in the NADH formed by reduction being oxidized again. Bergmeyer teaches that this NADH or formate oxidase action is not due to impurities, but is brought about by true side activities of the FDH. Consequently, the values obtained are always lower than the theoretical values. The proportionality factor must be ascertained anew for each enzyme preparation by calibration against a standard formate solution.

Also in the case of a *Candida* N-16 extract (Agr. Biol. Chem. 36, 2297/1972), it was found that in the case of incubation with formate and NAD, stoichiometry was not achieved due to side reactions.

It is an object of the present invention to overcome this disadvantage.

Surprisingly, we have found that FDH from *Candida boidinii* DSM 941 does not suffer from the disadvantage of the known FDH preparations and oxidises formate quantitatively to carbon dioxide with stoichiometric reduction of the hydrogen acceptor, according to the following equation, in which NAD is used as hydrogen acceptor:

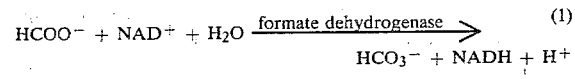

$$HCOO^- + NAD^+ + H_2O \xrightarrow{\text{formate dehydrogenase}} HCO_3^- + NADH + H^+ \quad (1)$$

Thus, according to the present invention, there is provided a process for the determination or removal of formate or of compounds convertible into formate, such as oxalate, by reaction in the presence of FDH and a hydrogen acceptor, wherein there is used FDH from *Candida boidinii* DSM 941.

Because of its quantitative reaction of formate, the process of the present invention can be used not only for the determination of formate but also for the removal of formate from solutions containing it, for example, in analytical or preparative work in which the presence of formate has a disturbing action.

The process of the present invention can also be employed for the determination of compounds convertible into formate, for example oxalate. Oxalate can, for example, be converted in known manner with oxalte decarboxylase into formate according to the following equation:

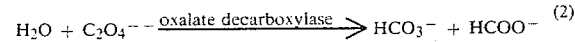

$$H_2O + C_2O_4^{--} \xrightarrow{\text{oxalate decarboxylase}} HCO_3^- + HCOO^- \quad (2)$$

Examples of other compounds convertible into formate, which can be determined according to the present invention, include formyl-CoA, formyl phosphate and formyl-tetrahydrofolic acid derivatives, as well as certain polyols after oxidative fission, for example with lead tetraacetate.

FDH from various *Candida boidinii* strains is known. Hitherto, for none of these enzymes could there be found the quantitative oxidation of the hydrogen acceptor present in the case of the enzyme employed according to the present invention. On the contrary, the enzymes previously obtained from the various *Candida boidinii* strains were found to be very similar to the enzyme obtained from *Pseudomonas oxalaticus* (Arch. Microbiol. 90, 263/1973).

The enzyme used in the process according to the present invention can be obtained from the micro-organism by methods known for obtaining FDH.

However, a process is preferred using a microorganism which has been cultured on methanol as a source of carbon, which is digested by autolysis and then treated with polyethyleneimine. The supernatent of the polyethyleneimine precipitation contains the desired enzyme, which can be adsorbed on phosphate gel and again extracted therefrom with phosphate buffer. The fraction thus obtained already has a specific activity of 1.3 to 1.4 U/mg. and can be used for formate determination. However, further purification is preferably carried out by ammonium sulphate fractionation and chromatography over weakly basic ion exchangers. Finally, a fine purification can be carried out by treatment with hydroxyapatite, which absorbs impurities still present without binding the FDH.

The reaction can be carried out at pH values at which the enzyme is active, i.e. from about 5.5 to 10 and preferably from 6.5 to 9.5. The buffer used is preferably a phosphate buffer although other buffers which are effective in the mentioned pH range can also be employed, such buffers being known in the art.

The *Candida boidinii* DSM 941 can be cultured by conventional methods, using media with a content of methanol, methanol being added to the medium in order adaptatively to achieve a higher content of FDH in the micro-organisms. An especially appropriate culture medium is described in Arch. Microbiol. 84, 29-42/1072, which consists essentially of yeast extract, malt extract, glucose and methanol.

Another medium which can be used contains, in addition to methanol and yeast extract, potassium, ammonium, magnesium, chloride, phosphate and sulphate ions, as well as trace elements.

The present invention also provides a reagent for the determination of formate or of compounds convertible into formate, which comprises formate dehydrogenase, a hydrogen acceptor and buffer, the formate dehydrogenase having been obtained from *Candida boidinii* DSM 941.

The reagent according to the present invention preferably contains NAD as the hydrogen acceptor. An especially preferred reagent according to the present invention consists essentially of 0.1 to 10 mMol/liter NAD, 10 to 250 mMol/liter and especially 25 to 100 mMol/liter phosphate buffer and 0.05 to 5 U/ml. formate dehydrogenase from *Candida boidinii* DSM 941, in each case referred to the aqueous solution of the reagent.

In addition, the reagent according to the present invention can also contain a stabilizer for the enzyme and/or for the hydrogen acceptor, such as NAD, a sequestering agent and possibly also a surface-active agent.

The present invention overcomes the disadvantages of the previously known processes for the determination of formate which, in particular, were due to the fact that the reaction with the hydrogen acceptor did not take place quantitatively. Therefore, the present invention permits the omission of the previously necessary determination of correction factors for the evaluation of the measurement results and is, therefore, also especially useful in automatic analyzers.

The following Example is given for the purpose of illustrating the present invention

EXAMPLE

Obtaining the enzyme 400 g. of *Candida boidinii* DSM 941, cultured on methanol and in a deep frozen state, were thawed out in 1200 ml. of 50 mM ammonium sulphate solution and kept for about 1 hour at 37° C. The suspension obtained was then mixed with a 10% polyethyleneimine solution (pH 7.5). The precipitate obtained was centrifuged off and the supernatant was mixed with 9 vol.% phosphate gel (pH 7.5) and, after 30 minutes, centrifuged. After washing with 0.5M aqueous sodium chloride solution, the gel was extracted with 0.2M phosphate buffer (pH 7.5). The extracts were mixed with 3.2M aqueous ammonium sulphate solution, while maintaining a pH value of 7.5. The precipitate formed was separated off and, after dissolving in phosphate buffer (pH 7.5), chromatographed over DEAEcellulose (cellulose modified with diethylaminoethanol units), elution being carried out with an increasing concentration of phosphate buffer (pH 7.5). The FDH-containing fractions were combined and again made 3.2M with regard to ammonium sulphate, while maintaining the pH value. The precipitate formed was separated off, dissolved in phosphate buffer (pH 7.5) and, after dialysis, treated with hydroxyapatite. After separating off the hydroxyapatite, the solution was lyophilised.

Yield: 0.7 g. lyophilisate with a specific activity of about 3.5 U/mg. protein, the total yield being about 43%.

Formate determination 0.02 ml. of a 0.100 mol/liter aqueous NAD solution, 0.02 ml. of 2.5 mMol/liter sodium formate solution and 0.8 ml. mol/liter phosphate buffer (pH 7.5) were mixed and made up with water to 1.0 ml.

In a comparison sample, the formate solution was replaced by the same amount of water. The initial extinction was then measured at 366 nm for both samples. Subsequently, the reaction was started by the addition of 0.2 U FDH. After 30 minutes, the end extinction was read off.

The result was calculated with the literature value for NADH of 3.4 cm$^2$/μmol. In 6 parallel experiments, there was obtained 0.0498 μmol (99.5% of the initial value) in the case of a variation coefficient of 1.28%. Therefore, the result was not statistically different from the value to be expected theoretically.

A comparative determination according to Example 4 of German Patent Specification No. 2,013,700 with the enzyme described therein gave, in the case of using 0.05 μmol. formate, a verification value 0.0468 μmol (93.6% of the actual value). The sole deviation from this Example 4 was that, analogously to the above Example, the NAD solution contained 0.100 mol/liter. This was necessary since, apparently due to a clerical error in the above-mentioned German Patent Specification, the amount of NAD mentioned therein would not have sufficed for the stoichiometric reaction of the formate present.

It will be understood that the specification and examples are illustrative, but not limitative of the present invention and that other embodiments within the spirit and scope of the invention will suggest themselves to those skilled in the art.

What is claimed is:

1. Process for the determination of a formate compound selected from formate, or a compound convertible into formate, which process comprises reacting said formate compound in the presence of formate dehydrogenase from *Candida boidinii* DSM 941 and a hydrogen acceptor, and then measuring the NADH formed as a measure of the formate compound initially present.

2. Process as claimed in claim 1 wherein the hydrogen acceptor is nicotinamide-adenosine-dinucleotide, and the formate compound initially present is measured by optically measuring the reduced dinucleotide formed in said process.

3. Process as claimed in claim 1 wherein said *Candida boidinii DSM 941* has been cultured on methanol as a carbon source.

4. Process as claimed in claim 1 wherein the reaction is carried out at a pH of from 5.5 to 10.

5. Process as claimed in claim 4 wherein the reaction is carried out at a pH of from 6.5 to 9.5

6. Process as claimed in claim 1 wherein said formate compound is oxalate.

7. Process for the removal of a formate compound selected from formate and compounds convertible into formate which process comprises reacting the composition containing formate in the presence of formate dehydrogenase from *Candida boidinii* DSM 941 and a hydrogen acceptor, whereby said formate is quantitatively converted.

8. Reagent for the determination of a formate compound selected from formate and compounds convertible into a formate, which reagent comprises formate dehydrogenase from *Candida boidinii* DSM 941 in an amount sufficient to react with the formate compound to be determined, and a hydrogen acceptor and a buffer in an amount sufficient to quantify the formate to be determined.

9. Reagent as claimed in claim 8 wherein the hydrogen acceptor is nicotinamide-adenosine-dinucleotide.

10. Reagent as claimed in claim 8 wherein the reagent comprises
   0.1 to 10 mMol/liter NAD,
   10 to 250 mMol/liter phosphate buffer, and
   0.05 to 5 U/ml formate dehydrogenase from
   *Candida boidinii* DSM 941, based on, in each case, to total aqueous solution reagent.

11. Reagent as claimed in claim 8 comprising from 25 to 100 mMol/liters of phosphate buffer.

12. Reagent as claimed in claim 8 also comprising a stabilizer compound to stabilize at least one of the formate dehydrogenase in the hydrogen acceptor.

13. Reagent as claimed in claim 8 also comprising a sequestering agent.

14. Reagent as claimed in claim 8 also comprising a surface active agent.

* * * * *